United States Patent
Klee et al.

(10) Patent No.: US 9,770,395 B2
(45) Date of Patent: *Sep. 26, 2017

(54) DENTAL ADHESIVE

(75) Inventors: Joachim E. Klee, Radolfzell (DE); Uwe Lehmann, Constance (DE)

(73) Assignee: Dentsply Detrey GmbH, Constance (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/584,858

(22) Filed: Sep. 14, 2009

(65) Prior Publication Data

US 2011/0306697 A1    Dec. 15, 2011

Related U.S. Application Data

(63) Continuation of application No. 12/148,572, filed on Apr. 21, 2008, now abandoned, which is a continuation of application No. 10/493,721, filed as application No. PCT/EP02/11940 on Oct. 25, 2002, now abandoned.

(60) Provisional application No. 60/345,994, filed on Oct. 26, 2001.

(30) Foreign Application Priority Data

Oct. 18, 2006    (WO) ................ PCT/EP2006/010051

(51) Int. Cl.
*A61K 6/087* (2006.01)
*A61K 6/00* (2006.01)

(52) U.S. Cl.
CPC .................................. *A61K 6/0023* (2013.01)

(58) Field of Classification Search
USPC ................ 523/118, 116; 433/228.1
See application file for complete search history.

(56) References Cited

U.S. PATENT DOCUMENTS

| | | | |
|---|---|---|---|
| 2,741,563 A * | 4/1956 | Robertson | C08K 5/092 106/270 |
| 3,709,866 A | 1/1973 | Waller | |
| 4,514,342 A | 4/1985 | Billington et al. | |
| 4,806,381 A | 2/1989 | Engelbrecht et al. | |
| 5,166,117 A | 11/1992 | Imai et al. | |
| 5,218,070 A | 6/1993 | Blackwell | |
| 5,320,886 A * | 6/1994 | Bowen | A61L 24/06 428/34.1 |
| 6,350,839 B2 | 2/2002 | Moszner | |
| 6,489,406 B1 | 12/2002 | Mahbub et al. | |
| 6,583,248 B1 | 6/2003 | Bowen | |
| 6,800,671 B1 | 10/2004 | Montgomery et al. | |
| 7,078,451 B2 * | 7/2006 | Hartman | C08K 3/22 523/514 |
| 7,226,960 B2 * | 6/2007 | Jia | 523/115 |
| 8,198,388 B2 * | 6/2012 | Klee et al. | 526/277 |
| 2003/0055124 A1 * | 3/2003 | Klee et al. | 523/120 |
| 2003/0152888 A1 | 8/2003 | Sun et al. | |

FOREIGN PATENT DOCUMENTS

| | | |
|---|---|---|
| DE | 2312559 | 9/1973 |
| EP | 0115410 B1 | 5/1987 |
| EP | 05115948 B1 | 10/1988 |
| EP | 0120559 B1 | 12/1988 |
| EP | 0219058 B1 | 6/1991 |
| EP | 0277413 B1 | 4/1992 |
| EP | 1548021 B1 | 6/1994 |
| EP | 0480472 B1 | 2/1996 |
| WO | 0248213 A1 | 6/2002 |
| WO | 2007045303 A1 | 4/2007 |
| WO | 2007045459 A1 | 4/2007 |

* cited by examiner

*Primary Examiner* — Tae H Yoon
(74) *Attorney, Agent, or Firm* — McNees Wallace & Nurick LLC

(57) ABSTRACT

Non-aqueous dental adhesive comprising a mixture containing (i) one or more polymerizable monomers optionally containing an acidic group, (ii) a polymerization initiator, and (iii) a thermal polymerization inhibitor of the following formula (I)

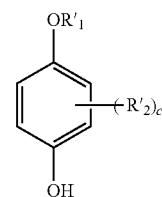

wherein
$R'_1$ represents a hydrogen atom, or a saturated hydrocarbon group having 1 to 18 carbon atoms. $R'_2$, which may be the same or different if more than one $R'_2$ is present, independently represent a saturated hydrocarbon group having 1 to 18 carbon atoms, and c represents an integer of from 1 to 4, and (iv) optionally an organic solvent.

18 Claims, 8 Drawing Sheets

| Component | Content (wt.-%) |
|---|---|
| BAP | 63.2 |
| BAA-TCD | 21.1 |
| DHPOBA_analog | 54.2 |
| 2-Acrylamido-2-methyl-propanesulfonic acid (AMPS) | 43.8 |
| Camphor Quinone | 1.3 |
| TPO | 3.2 |
| DMABE | 1.5 |
| Total | 100.00 |
| | |
| Active Matrix | 55 |
| Acrylic acid | 9 |
| Water | 36 |
| Total | 100 |

FIG. 1

DENTAL ADHESIVE

REFERENCE TO RELATED APPLICATIONS

This application is a continuation of U.S. patent application Ser. No. 12/148,572, filed Apr. 21, 2008 and entitled "Dental adhesive", now abandoned, which is a continuation of U.S. patent application Ser. No. 10/493,721, filed Apr. 26, 2004 and entitled "Hydrolysis stable self-etching, self-priming adhesive", now abandoned, which is a national stage entry of PCT Patent Application No. PCT/EP02/11940, filed Oct. 25, 2002 and entitled "Hydrolysis stable self-etching, self-priming adhesive", now expired, which claims priority from U.S. Provisional Patent Application No. 60/345,994, filed Oct. 26, 2001.

FIELD OF THE INVENTION

The present invention relates to a dental adhesive having improved storage stability and low toxicity The dental adhesive may be a one-pack dental adhesive composition, in particular a total etch dental adhesive The present invention also relates to the use of a specific thermal polymerization inhibitor in a dental adhesive composition.

BACKGROUND OF THE INVENTION

Dental adhesive compositions known from the prior art typically contain a mixture of a polymenzable monomer and an initiator system in a suitable solvent. The activity of the polymerizable monomers and the initiator system of the mixture must be adapted to provide sufficient curing activity and adhesion on dentin and enamel surfaces However, an increased activity leads to a complex stability problem during storage of the components of the mixture Specifically, the initiator system may be activated leading to premature polymerization of the mixture.

As a result of the stability problem of the mixture, the storage stability at room temperature of commercial dental adhesive compositions known from the prior art may be insufficient For example, conventional commercial one-part self-etching, self-priming dental adhesive compositions must be stored in a refrigerator in order to avoid deterioration by solvolysis or polymerization The commercial composition "iBond Gluma inside" may be mentioned, which has a low thermal stability when stored at temperatures of 37° C. or 50° C. due to premature polymerization within less than two weeks, which is indicative of an insufficient thermal stability at room temperature for all practical purposes. Similar stability problems are observed with other dental adhesive compositions.

EP-A 1 548 021 suggests hydrolysis stable one-part self-etching, self-priming dental adhesive compositions containing specific monomers having improved resistance against hydrolysis under acidic conditions In order to improve the stability of the initiator system, EP-A 1 548 021 suggests a stabilizer such as hydroquinone monomethylether, 2,6-di-tert.-butyl-p-cresol, tetramethyl piperidine N-oxyl radical and galvanoxyl radical. However, generic one-part self-etching, self-priming dental adhesive composition known from EP-A 1 548 021 still require improvement of the thermal stability at storage for attaining a stability of at least 10 days at 60° C. required. Moreover, hydroquinone is an allergenic compound imparting undesirable toxic properties to a dental adhesive composition.

SUMMARY OF THE INVENTION

It is a problem of the present invention to provide a dental adhesive composition having a low toxicity and thermal stability at storage of at least 10 days at 60° C.

Moreover, it is the problem of the present invention to provide a specific class of compounds which may be used to stabilize a dental adhesive composition for at least 20 days during storage at 60° C.

The present invention provides a non-aqueous dental adhesive comprising a mixture containing:
(i) one or more polymerizable monomers optionally containing an acidic group,
(ii) a polymerization initiator,
(iii) a thermal polymerization inhibitor of the following formula (I):

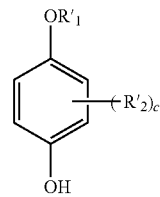

wherein
R\ represents a hydrogen atom, or a saturated hydrocarbon group having 1 to 18 carbon atoms.
$R'_2$, which may be the same or different if more than one $R'_2$ is present, independently represent
a saturated hydrocarbon group having 1 to 18 carbon atoms, and c represents an integer of from 1 to 4, and (iv) optionally an organic solvent.

The present invention is based on the recognition that a mixture containing one or more polymerizable monomers optionally containing an acidic group, one or more organic or inorganic acids, and a polymerization initiator is problematic with regard to polymerization whereby conventional stabilizers such as hydroquinone monomethylether, 2,6-di-tert.-butyl-p-cresol, tetramethyl piperidine N-oxyl radical and galvanoxyl radical provide an insufficient effect for attaining a high storage stability.

The present invention is furthermore based on the recognition that a specific class of water insoluble stabilizers provides a surprising stabilizing effect so that a dental adhesive may be provided which has an excellent storage stability due to an improved resistance against premature polymerization.

Accordingly, the present invention also relates to the use of a compound of the following formula (I):

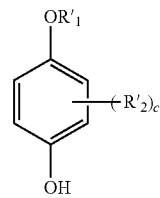

wherein
$R^1$, represents a hydrogen atom, or a saturated hydrocarbon group having 1 to 18 carbon atoms.
$R'_2$, which may be the same or different if more than one $R'_2$ is present, independently represent a saturated hydrocarbon group having 1 to 18 carbon atoms, and c represents an integer of from 1 to 4, as a thermal polymerization inhibitor in a dental composition.

BRIEF DESCRIPTION OF THE DRAWINGS

FIG. 1 shows a dental adhesive composition according to the present invention.

DESCRIPTION OF THE PREFERRED EMBODIMENTS

Figure 2:
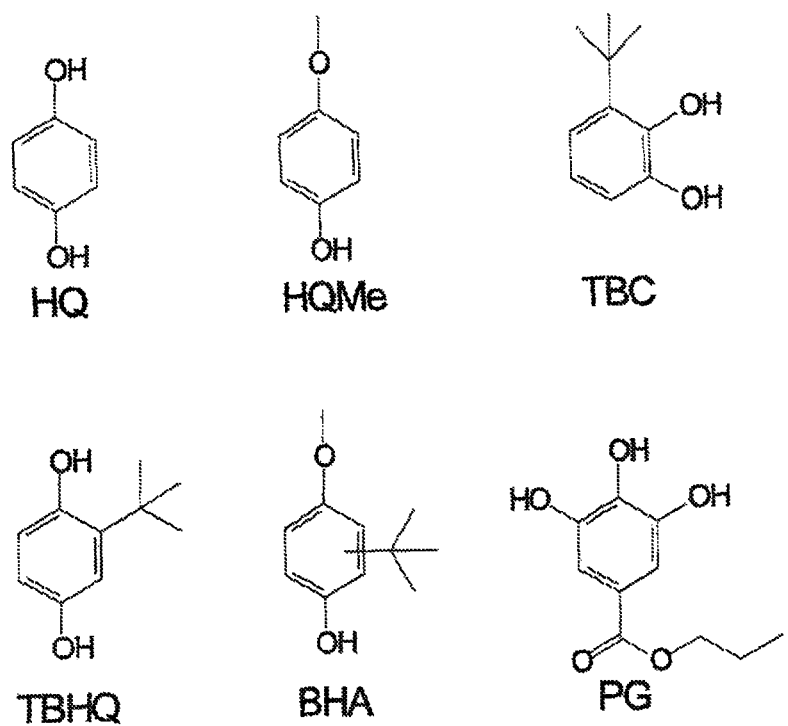
FIG. 2 shows the chemical structure of compounds tested as inhibitors.

The dental adhesive composition according to the present invention contains a water-insoluble thermal polymerization inhibitor of formula (I). Preferably, the saturated hydrocarbon group which may be present as R'., or R'$_2$ in formula (I) represents a straight chain or branched C$_{1-18}$ alkyl group or a C$_{3-18}$ cycloalkyl group optionally substituted by one or more C$_{1-5}$ alkyl groups or a C$_{4-18}$ cycloalkylalkyl group optionally substituted by one or more C$_{1-5}$ alkyl groups.

Preferably, R$^1$, represents a straight chain or branched C$_{1-18}$ alkyl group. In a preferred embodiment, R\ is hydrogen or a tert.-butyl group.

R'$_2$ in formula (I) is believed to provide a steric effect due to the bulky nature of the substituent in this position. Therefore, at least one R'$_2$ in formula (I) is a saturated hydrocarbon group having 1 to 18 carbon atoms. Accordingly, in a specific embodiment, at least one R'$_2$ in formula (I) represents a branched C$_{3-18}$ alkyl group or a C$_{3-18}$ cycloalkyl group optionally substituted by one or more C$_{1-6}$ alkyl groups or a C$_{4-18}$ cycloalkylalkyl group optionally substituted by one or more C$_{1-5}$alkyl groups. More specifically, at least one R'$_2$ in formula (I) preferably represents a branched C$_{3-18}$ alkyl group or a C$_{3-18}$ cycloalkyl group optionally substituted by one or more C$_{1-5}$ alkyl groups. Even more specifically, at least one R'$_2$ in formula (I) preferably represents a branched C$_{3-18}$ alkyl group. In a further preferred embodiment, R'$_2$ is a tert.-butyl group.

c represents an integer of from 1 to 4, preferably 1 or 2. In a specific embodiment, c is 1.

Preferably, thermal polymerization inhibitor is a compound of the following formula (I$^1$):

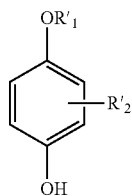

wherein
R\ represents a hydrogen atom, or a saturated hydrocarbon group having 1 to 18 carbon atoms; R'$_2$ represents a saturated hydrocarbon group having 1 to 18 carbon atoms. Most preferably, the inhibitor is tert.-butyl hydroquinone (TBHQ) or tert.-butyl hydroxyanisole (BHA).

Preferably, the inhibitor is contained in the dental adhesive composition in an amount of from 0.01 to 0.5 mol %, more preferably in an amount of from 0.05 to 0.3 mol %.

The dental adhesive composition according to the present invention contains a polymerizable monomers optionally containing an acidic group.

The polymerizable monomers in the dental adhesive composition according to the invention are capable of free-radical polymerization and are preferably (meth)acrylate monomers or oligomers. The dental adhesive according to the invention may contain a polymerizable monomer or oligomer as a mixture of different compounds or as isomers of the same compound. The polymerizable monomer or oligomer may include a derivative of at least one unsaturated carboxylic acid selected from the group consisting of acrylic acid, methacrylic acid, cyanoacrylic acid and itaconic acid, and mixtures thereof, a derivative of styrene, or a polymerizable moiety containing a carbon-carbon double bond conjugated with a carbonyl group.

The (meth)acrylate monomer or oligomer is selected from materials having at least one, and preferably two to four polymerizable double bonds per molecule so that the cured dental adhesive be crosslinked and thus better suited for use in the oral cavity. Monomers with a single polymerizable double-bond may be used in order to adjust the viscosity of the composition. (Meth)acrylate monomer materials useful herein are well known in the art. The preferred materials generally include monomers having a central portion containing an organic moiety and at least two (meth)acrylic end groups. Desirable characteristics for such monomers and/or oligomers include good film forming properties, low viscosity, low polymerization shrinkage, low water sorption and the ability to cure rapidly and completely in the mouth. It is also desirable that the monomers be low in volatility and non-irritating to the tooth pulp. A mixture of two or more appropriate methacrylate monomers is within the scope of this invention. In fact, depending on the choice of monomers, mixture are often highly desirable to optimize the characteristics of the resulting dental composition.

The polymerizable monomer or oligomer may also be selected from the group consisting of hydroxyethyl acrylate, hydroxypropyl acrylate, diurethane dimethacrylate resin, hydroxyethyl methacrylate, hydroxypropyl methacrylate, trimethylolpropane triacrylate, 1,6-hexanediacrylate, glycerin diacrylate, triethyleneglycol diacrylate, tetraethyleneglycol diacrylate, and 2-acrylamido^-methyM-propansulfonic acid, a reaction product of butane tetracarboxylic acid dianhydride and hydroxyethylmethacrylate, triethyleneglycol dimethacrylate, urethane dimethacrylate, and a reaction product of butane tetracarboxylic acid dianhydride and glycerol dimethacrylate, or acrylamides or derivatives thereof such as 2-acrylamido-2-methylpropane sulphonic acid, N,N-methylene-bis-acrylamide, N,N-ethylene-bis-acrylamide, and 1,3-bis(acrylamido)-N,N-diethylpropane The polymenzable monomer or oligomer may be a phosphate based acid adhesion promoter selected from the group consisting of phosphate ester or phosphonate derivatives of radical polymenzable alcohol or polyol derivatives The phosphate ester derivatives may be prepared using the method given in U.S. Pat. No. 4,514,342 As examples of suitable carboxylic acid based adhesion promoters may be mentioned the reaction product between butanetetracarboxylic acid dianhydride and hydroxyethyl acrylate as in U.S. Pat. No. 5,218,070 Various radical polymerizable acidic monomers useful as adhesion promoters may also be obtained by many other means, for instance as given in U.S. Pat. No. 4,806,381 and U.S. Pat. No. 6,350,839

The polymerizable monomer or oligomer may further be a carboxylic acid based adhesion promoter selected from the group consisting of reaction products between acid anhydrides and radical polymerizable derivatives of alcohols The acid anhydride may be selected from the group consisting of butanetetracarboxylic acid dianhydride, tetrahydrofurantetracarboxylic acid dianhydride, benzenetetracarboxylic acid dianhydride and benzentricarboxylic acid anhydride The radical polymerizable derivatives of alcohols may be selected from the group consisting of hydroxyethyl acrylate, hydroxypropyl acrylate, glycerol diacrylate, pentaerythritol triacrylate, dipentaerythritol pentaacrylate, hexanediol acrylate, polyethylenoxide acrylate, and trial Iy pentaeryth πtol composition was used as follows: See FIG. 1.

These may be mono- or polyfunctional acrylates and methacrylates of the kind described, for example, in EP-A-0 480 472 Moreover, functionalized monomers with terminal acrylate or methacrylate groups may likewise be used, of the kind described, e g, in DE-A-2 312 559 and in EP-A-0 219 058.

The dental adhesive according to the present invention may contain polymerizable monomers in an amount of from 5 to 90 wt-%, preferably in an amount of from 20 to 70 wt %.

It is preferred that the monomer or oligomer or monomer or oligomer blend has a viscosity of at most 100 Pas at 23° C., more preferably at most 5 Pas.

The dental adhesive composition according to the invention may optionally comprise an organic solvent. In a preferred embodiment, the dental adhesive contains one or more further solvents selected from conventional inert solvents such as short-chain alcohols, short-chain ketones, aliphatic or unsaturated ethers, and cyclic ethers conventionally used in the dental field. Preferred solvents are selected from acetone, ethanol and t-butanol. The dental adhesive composition may contain the solvent in an amount of from 10 to 95 wt. %.

The dental adhesive composition according to the present invention may further comprise an initiator. A chemical initiator may be used in case of a multicomponent composition. The chemical initiator is able to form radicals by mixing at least two chemically different substances, which have to be stored separately, without a further input of energy, which radicals are then able to initiate a polymerization reaction. Examples of such chemical initiator systems are peroxy amine or peroxy proton donor/metal compound mixtures, of the kind described by J. M. Antonucci et al. in J. Dental Research (1979), 58 (9), page 1887-1889 or in U.S. Pat. No. 5,166,117 and in EP-A-O 115 410, 0 115 948, 0 120 559 and 0 277 413. More preferred are initiators capable of forming radicals without mixing of different components, but based on input of energy such as thermal or light energy. In this case, the dental adhesive composition may be a one-component dental adhesive composition, wherein the initiator is a photoinitiator and/or a thermal initiator. The composition may comprise an alpha-diketone such as camphor quinone.

The dental adhesive may further contains an inorganic filler and/or an organic filler; preferably the filler is a nanofiller. A filler may be contained in an amount of from 0.5 to 20 wt. %, more preferably 2 to 10 wt. %.

A one-pack composition means that the composition of the present invention is contained in only one container which may be stored and allows application of the composition without any mixing and without any special equipment before the application.

A total etch composition is a one-pack composition having priming and bonding activity on a dental surface such as dentin or enamel.

The invention will now be further illustrated with reference to the following examples:

EXAMPLES

Test Formulation Containing Different Inhibitors

A series of test formulations containing different thermal polymerization inhibitors was prepared in order to illustrate the surprising thermal stability of a dental adhesive composition according to the present invention. The standard composition was used as follows: See FIG. 1.

The following comparative inhibitors were tested:
(i) hydroquinone (HQ),
(ii) hydroquinone monomethylether (HQME),
(iii) bisphenol A,
(iv) propyl gallate (PG)

The following inhibitors according to the present invention were tested: (vii) tert-Butylhydroquinone (TBHQ), and (viii) tert.-Butylhydroxyanisol (BHA). (FIG. 2)

Test formulations containing different inhibitors or inhibitor concentrations were stored in Prime&Bond NT bottles (Dentsply DeTrey) at 60° C. until thermal polymerization. The bottles were daily examined by shaking the bottle, whereby the acoustical test turned out to be rather sensitive, and by taking a sample with a pipette. When polymerization seemed to have occurred or after a certain minimum storage time (20 days) the bottles were sliced open and the solution were examined visually.

According to the results of the above described Arrhenius investigation at least a thermal stability of about 11 days at 60° C. is necessary so that the dental adhesive composition may be stored at room temperature.

Results

The Test Formulation containing different inhibitors in different amounts, was investigated regarding its thermal stability by storing these formulations at 60° C. The samples were daily examined. In case of polymerization a gel or a solid, polymerized body was observed.

The dark shaded columns represent formulations with inhibitors, respectively inhibitor concentrations, which were polymerized after the depicted time at 60° C. The light shaded columns represent formulations, which were not polymerized until the depicted time. Usually after 20 days the investigation was terminated.

Figure 3:
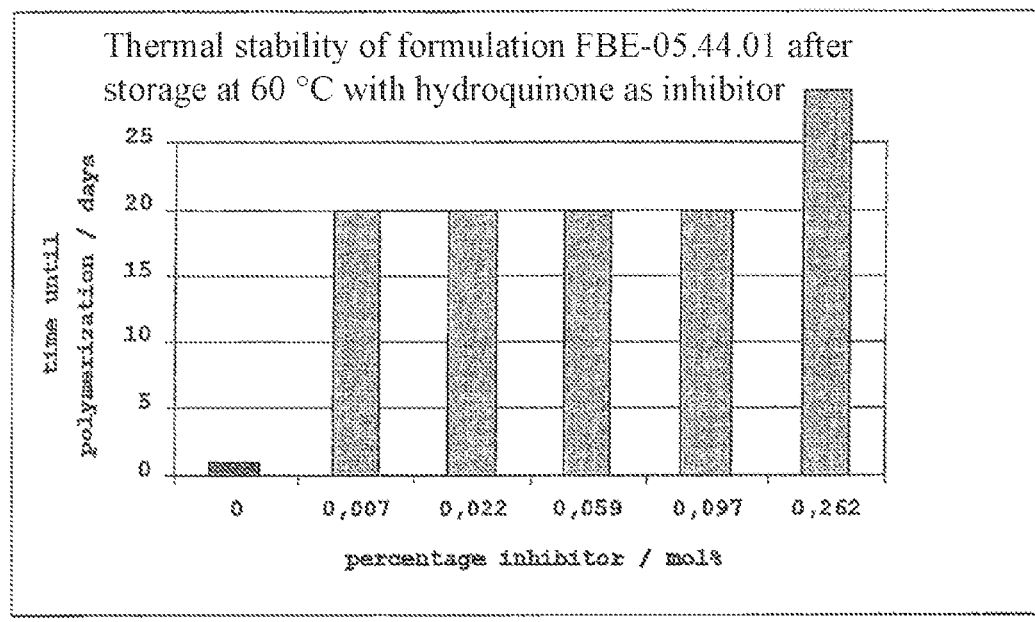
FIG. 3 shows thermal stability results with hydroquinone (HQ) as the inhibitor.
Figure 4:
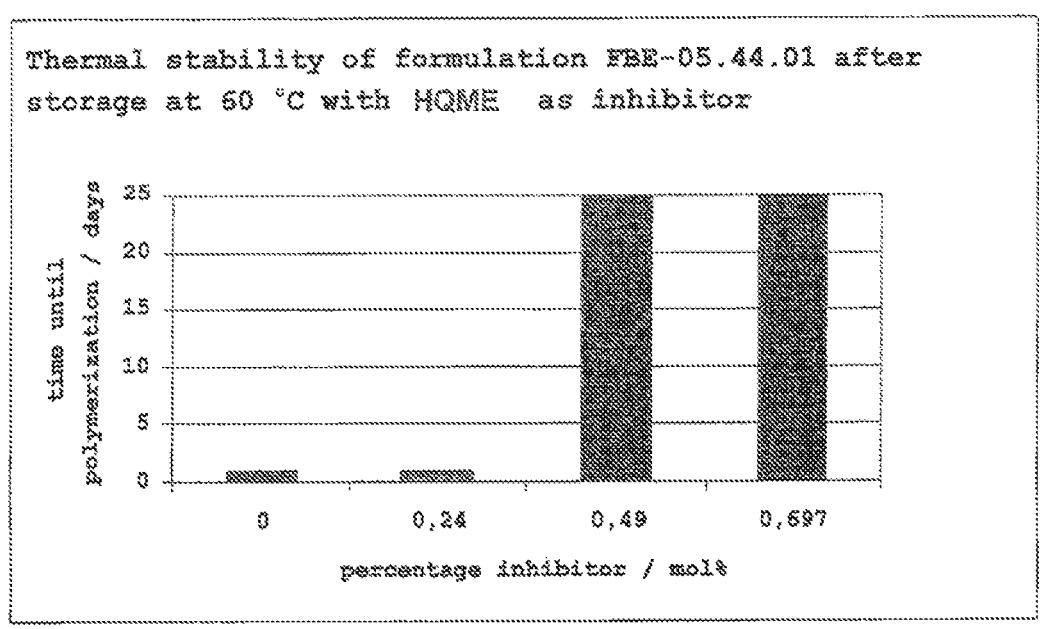
FIG. 4 shows thermal stability results with hydroquinone monomethylether (HQME) as the inhibitor.

In the comparison, hydroquinone (HQ) was used in an amount of 0.15 mol % showing some stabilization effect. However, hydroquinone is an allergenic compound and therefore undesirable for use in a generic dental composition. Hydroquinone monomethylether (HQME) as well as BHT failed to provide a sufficient thermal stability.
(i) Hydrochinone (HQ)—Reference Inhibitor The results are shown in FIG. 3. Light shaded columns indicate that the formulation is not polymerized up to the recorded time; the dark shaded column shows a formulation polymerized after the recorded time.
(ii) Hydrochinone Monomethylether (HQME)—Reference Inhibitor The results are shown in FIG. 4.

After slicing open the samples containing 0.49 and 0.697 mol % HQME, small pieces of gel were found at the bottom, which were not detected before by shaking or by the examination with the pipette.

After slicing open the sample with 0.193 mol % TBC some pieces of gel were found at the bottom, which were not detected before by shaking or by the examination with the pipette.

(iii) Bisphenol A—Reference Inhibitor

Figure 5:
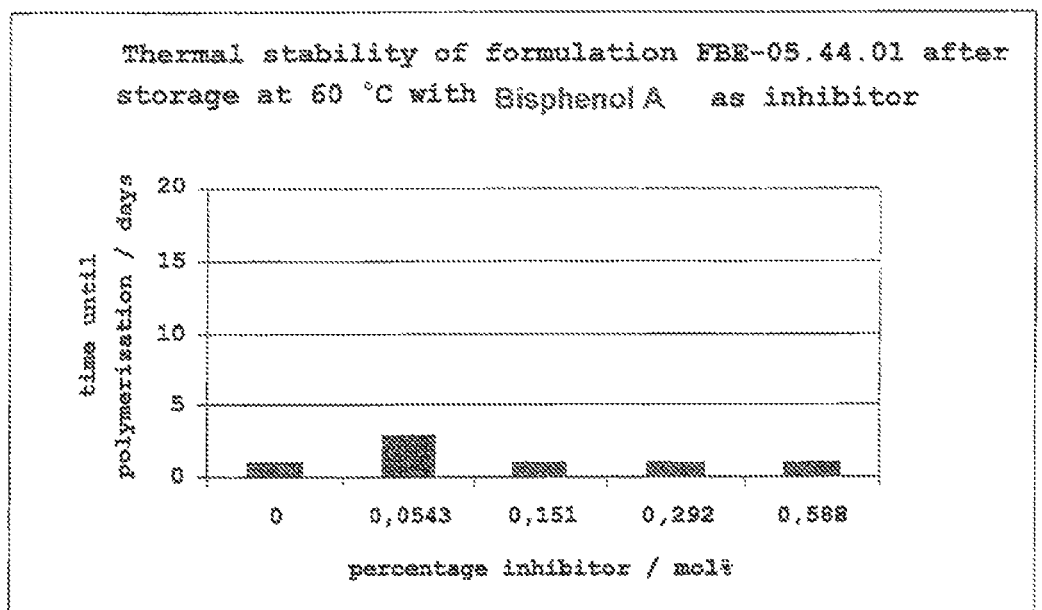
FIG. 5 shows thermal stability results with Bisphenol A as the inhibitor.

The results are shown in FIG. 5. The dark shaded columns indicate that the formulation is polymerized after the recorded time.

(iv) Propyl gal late (PG)—Reference Inhibitor

Figure 6:
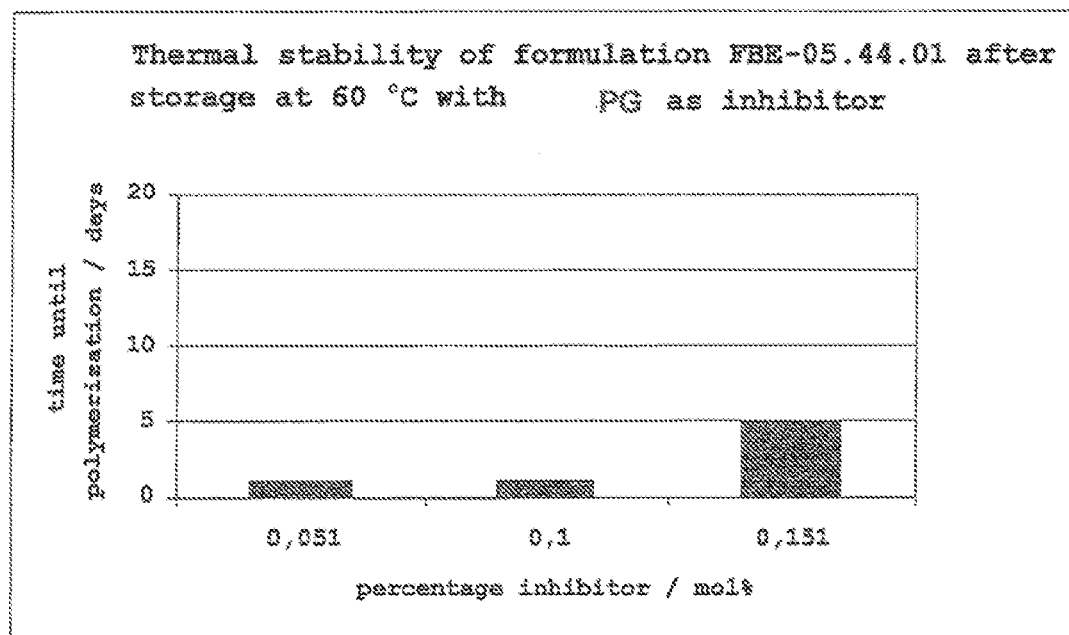
FIG. 6 shows thermal stability results with propyl gallate (PG) as the inhibitor.

The results are shown in FIG. 6 The dark shaded columns indicate that the formulation is polymerized after the recorded time.

(vii) tert.Butylhydroquinone (TBHQ)—Inhibitor of the Invention

Figure 7:
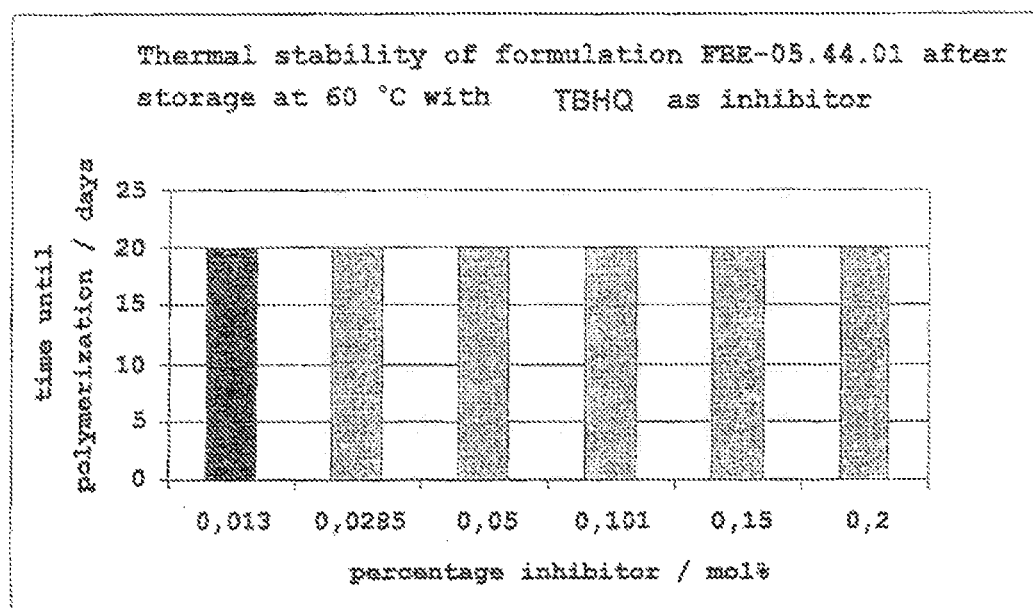
FIG. 7 shows thermal stability results with tert.-butyl hydroquinone (TBHQ) as the inhibitor.

The results are shown on FIG. 7.

After 14 days and after 20 days at 60° C. the bottles were sliced open, the contents was investigated and filled in a new bottle, which was stored again at 60° C. No hints of a polymerization were found After 20 days at 60° C. the bottles were sliced open again and the contents was investigated Only in case of the lowest TBHQ percentage of 0 013 mol % polymerization was found. This was not detected before by the daily examination.

(viii) tert.-Butylhydroxyanisole (BHA)—Inhibitor of the Invention

Figure 8:
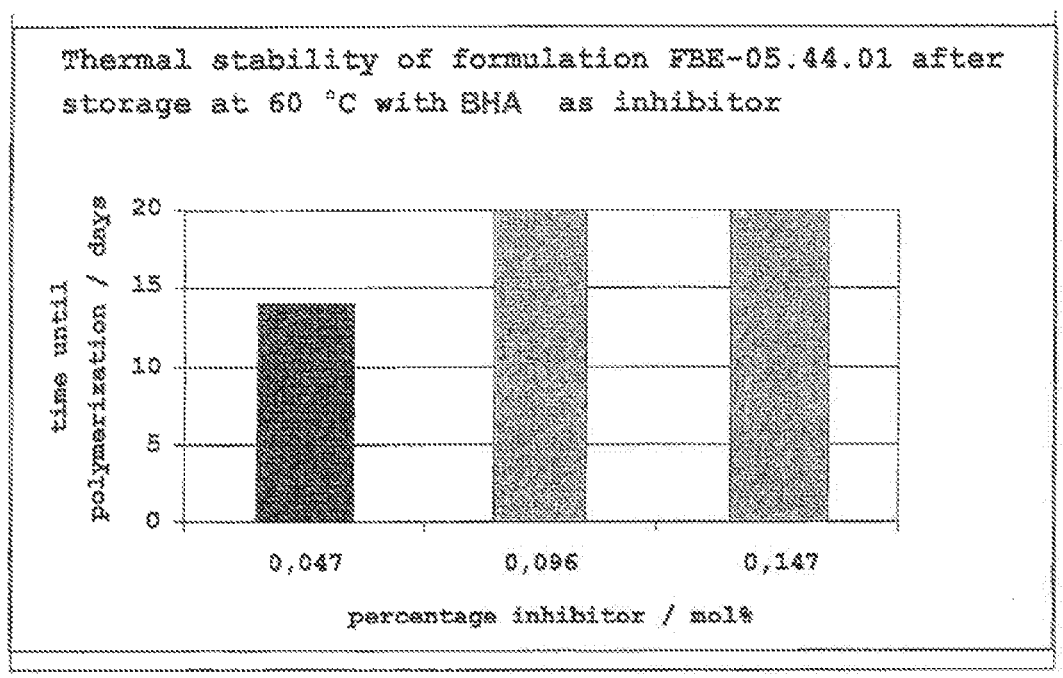
FIG. 8 shows thermal stability results with tert.-butyl hydroxyanisole (BHA) as the inhibitor.

The results are shown in FIG. 8.

After 14 days at 60° C. all bottles were sliced open, the contents was investigated and filled in a new bottle, which was stored again at 60° C. The sample with 0.047 mol % showed after 14 days at 60° C. some pieces of gel, which were not detected before by shaking or by the examination with the pipette After 20 days at 60° C. the bottles were again sliced open. No indication of polymerization for the samples containing 0.096 mol % and 0.147 mol % were found. The formulation with 0.047 mol % again contains some small pieces of gel.

Example 1

The following non-aqueous compositions were prepared with different amounts of TBHQ as an inhibitor. The compositions were stored at 65° C. The time required for polymerization and therefore deterioration of the composition was determined.

|  | Composition/wt.-% | | | |
| --- | --- | --- | --- | --- |
| Polymerizable Resins | 67.33 | 67.29 | 67.25 | 67.21 |
| CQ/Amine | 2.67 | 2.67 | 2.67 | 2.67 |
| TBHQ | 0.04 | 0.08 | 0.12 | 0.16 |
| Nanofiller | 5.47 | 5.47 | 5.47 | 5.47 |
| t-Butanol | 24.5 | 24.5 | 24.5 | 24.5 |
| Sum | 100 | 100 | 100 | 100 |
|  | Days life to polymerization | | | |
| Temp./° C. | t/d | t/d | t/d | t/d |
| 65 | 4 | 10 | 77 | >77 |

It was found that 0.028-0.2 mol % TBHQ provides a sufficient thermal stability over 20 days at 65° C.

Comparison Example 1

The following non-aqueous compositions were prepared with different amounts of BHT as an inhibitor. The compositions were stored at 65° C. The time required for polymerization and therefore deterioration of the composition was determined.

|  | Composition/wt.-% | | | |
| --- | --- | --- | --- | --- |
| Polymerizable Resins | 35.35 | 66.87 | 68.11 | 53.15 |
| CQ/Amine | 1.41 | 2.67 | 1.43 | 2.12 |
| BHT | 0.26 | 0.49 | 0.49 | 0.39 |
| Nanofiller | 2.89 | 5.47 | 5.47 | 4.35 |
| t-Butanol | 60.09 | 24.50 | 24.50 | 40 |
| Sum | 100 | 100 | 100 | 100 |
|  | Days life to polymerization | | | |
| Temp./° C. | t/d | t/d | t/d | t/d |
| 65 | 1 | 1 | 6 | 4 |

It was found that 0.028-0.2 mol % BHT does not provide a sufficient thermal stability over 20 days at 65° C.

Comparison Example 2

The following non-aqueous compositions were prepared with different amounts of PG as an inhibitor. The compositions were stored at 65° C. The time required for polymerization and therefore deterioration of the composition was determined.

|  | Composition/wt.-% | | | |
| --- | --- | --- | --- | --- |
| Polymerizable Resins | 67.31 | 67.26 | 67.21 | 67.16 |
| CQ/Amine | 2.67 | 2.67 | 2.67 | 2.67 |
| PG | 0.05 | 0.10 | 0.15 | 0.2 |
| Nanofiller | 5.47 | 5.47 | 5.47 | 5.47 |
| t-Butanol | 24.5 | 24.5 | 24.5 | 24.5 |
| Sum | 100 | 100 | 100 | 100 |
|  | Days life to polymerization | | | |
| Temp./° C. | t/d | t/d | t/d | t/d |
| 65 | 0-3 | 0-3 | 0-3 | 0-3 |

It was found that 0.028-0.2 mol % PG does not provide a sufficient thermal stability over 20 days at 65° C.

Example 2

0.6945 g N,N'-Bisacrylamido-N,N'-diethyl-1,3-propane, 0.2315 g 3,(4)$_1$8,(9)-bis(acrylamido methyl)tricyclo-5.2.1.0$^{2\beta}$ decane, 0.0595 g Ethyl 2-[12-dihydrogen phosphoryl-12,2-dioxamidecyljacrylate, 0.0481 g 2-Acrylamido-2-methyl-propane-sulfonic acid, 0.0141 g camphor quinone, 0.0355 g bis(2,4,6-trimethylbenzoyl)-phenyl phosphine oxide, 0.0164 g dimethylamino benzoic acid ethyl ester and 0.003 g 2-tert-Butylhydroquinone were dissolved in a solvent mixture composed of 0.1800 g acrylic acid and 0.7200 g water.

The adhesive does not polymerise after storage for 20 days at 60° C.

Example 3

0.6940 g N,N'-Bisacrylamido-N,N'-diethyl-1,3-propane, 0.2313 g 3,(4),8,(9)-bis(acrylamido methyl)tricyclo-5.2.1.0$^2$ $_6$ decane, 0.0595 g Ethyl 2-[12-dihydrogen phosphoryl-12,2-dioxamidecyl]acrylate, 0.0481 g 2-Acrylamido-2-methyl-propane-sulfonic acid, 0.0141 g camphor quinone, 0.0355 g bis(2,4,6-trimethylbenzoyl)-phenyl phosphine oxide, 0.0164 g dimethylamino benzoic acid ethyl ester and 0.0011 g 2-tert.-butyl-4-methoxyphenol were dissolved in a solvent mixture composed of 0.1800 g acrylic acid and 0.7200 g water. The adhesive does not polymerise after storage for 20 days at 60° C.

Comparative Example 3

0.6931 g N,N'-Bisacrylamido-N,N'-diethyl-1,3-propane, 0.231 O g 3,(4),8,(9)-bis(acrylamido methyl)tricyclo-5.2.1.0$^2$ $^6$ decane, 0.0594 g ethyl 2-[12-dihydrogen phosphoryl-12,2-dioxamidecyl]acrylate, 0.0480 g 2-Acrylamido-2-methyl-propane-sulfonic acid, 0.0141 g camphor quinone, 0.0354 g bis (2,4,6-trimethylbenzoyl)-phenyl phosphine oxide, 0.0164 g dimethylamino benzoic acid ethyl ester and 0.0026 g hydroquinone monomethyl ether were dissolved in a solvent mixture composed of 0.1800 g acrylic acid and 0.7200 g water. The adhesive polymerises after storage for 1 day at 60° C.

Comparative Example 4

0.6882 g N,N'-Bisacrylamido-N,N'-diethyl-1,3-propane, 0.2294 g 3,(4),8,(9)-bis(acrylamido methyl)tricyclo-5.2.1.0$^{26}$ decane, 0.0590 g Ethyl 2-[12-dihydrogen phosphoryl-12,2-dioxamidecyl]acrylate, 0.0477 g 2-Acrylamido-2-methyl-propane-sulfonic acid, 0.0140 g camphor quinone, 0.0352 g bis(2,4,6-trimethylbenzoyl)-phenyl phosphine oxide, 0.0162 g dimethylamino benzoic acid ethyl ester and 0.0103 g 2,6-di-tert.-butyl-4-cresol were dissolved in a solvent mixture composed of 0.1800 g acrylic acid and 0.7200 g water. The adhesive polymerises after storage for 2 days at 60° C.

It was found that 0.028-0.2 mol % TBHQ provides a sufficient thermal stability over 20 days at 65° C.

The invention claimed is:

1. A non-aqueous dental adhesive comprising a mixture containing:
   (i) one or more polymerizable monomers containing an acid group, which are selected from the group consisting of:
      2-acrylamido-2-methylpropane sulphonic acid; and
      phosphate ester or phosphonate derivatives of radical polymerizable alcohol or polyol derivatives,
   (ii) a polymerization initiator,
   (iii) a thermal polymerization inhibitor comprising tert.-butyl hydroquinone (TBHQ) or tert.-butyl hydroxyanisole (BHA), and
   (iv) optionally an organic solvent;
   wherein the thermal polymerization inhibitor is present at a concentration such that the non-aqueous dental adhesive is stable at storage for at least 10 days at 60° C.

2. The dental adhesive according to claim 1, wherein the thermal polymerization inhibitor is tert.-butyl hydroxyanisole (BHA).

3. The dental adhesive according to claim 1, further containing an organic water soluble solvent selected from the group consisting of alcohols and ketones.

4. The dental adhesive according to claim 1, wherein said polymerization initiator is a photo initiator.

5. The dental adhesive according to claim 1, which further contains an inorganic filler and/or an organic filler.

6. A method of using a compound comprising a non-aqueous mixture containing:
   (i) one or more polymerizable monomers containing an acid group, which are selected from the group consisting of:
      2-acrylamido-2-methylpropane sulphonic acid; and
      phosphate ester or phosphonate derivatives of radical polymerizable alcohol or polyol derivatives,
   the one or more polymerizable monomers being present in an amount from 20 to 70 wt % of the compound;
   (ii) a thermal polymerization inhibitor comprising tert.-butyl hydroquinone (TBHQ);
   (iii) a polymerization initiator comprising camphorquinone;
   (iv) a solvent comprising t.butanol; and
   (v) a nanofiller present in an amount from 2 to 10 wt % of the compound;
   wherein the thermal polymerization inhibitor is present at a concentration such that the mixture is stable at storage for at least 10 days at 60° C.

7. The dental adhesive according to claim 3, wherein the organic water soluble solvent is ethanol, propanol, butanol, acetone, methyl ethyl ketone, or any combination thereof.

8. The dental adhesive according to claim 4, wherein the polymerization initiator is camphorquinone.

9. The dental adhesive according to claim 5, wherein the inorganic filler and/or the organic filler is a nanofiller.

10. The dental adhesive according to claim 1, wherein the polymerization initiator is camphorquinone, the thermal polymerization inhibitor is tert.-butyl hydroquinone (TBHQ), and the solvent is t.butanol; and which further contains a nanofiller.

11. The dental adhesive according to claim 1, wherein the one or more polymerizable monomers containing an acid group comprises 2-acrylamido-2-methylpropane sulphonic acid.

12. The dental adhesive according to claim 1, wherein the thermal polymerization inhibitor is tert.-butyl hydroquinone (TBHQ).

13. The dental adhesive according to claim 1, wherein the thermal polymerization inhibitor is present in an amount in the range of 0.08 to 0.16% by weight of the mixture.

14. A non-aqueous dental adhesive comprising a mixture containing:
   (i) one or more polymerizable monomers comprising (meth)acrylate, the one or more polymerizable monomers being capable of free radical polymerization, being phosphate-based acid adhesion promoters, and containing an acid group, selected from the group consisting of:
      2-acrylamido-2-methylpropane sulphonic acid; and
      phosphate ester or phosphonate derivatives of radical polymerizable alcohol or polyol derivatives;
   (ii) a polymerization initiator comprising camphorquinone;
   (iii) a thermal polymerization inhibitor comprising tert.-butyl hydroquinone (TBHQ) in an amount less than or equal to 0.16% by weight of the mixture;
   (iv) a nanofiller; and
   (iv) an organic solvent comprising t-butanol;

wherein the non-aqueous dental adhesive is stable at storage for at least 10 days at 60° C.

15. The non-aqueous dental adhesive of claim 14, wherein the thermal polymerization inhibitor is present in an amount in the range of 0.08 to 0.16% by weight of the mixture.

16. The non-aqueous dental adhesive of claim 15, wherein the nanofiller is present at about 5.5% by weight of the mixture.

17. The non-aqueous dental adhesive of claim 16, wherein the organic solvent is present at about 24.5% by weight of the mixture.

18. The non-aqueous dental adhesive of claim 17, wherein the camphorquinone is present at about 2.7% by weight of the mixture and the one or more polymerizable monomers are present at about 67.2 to 67.3% by weight of the mixture.

* * * * *